United States Patent
Iaccino et al.

(10) Patent No.: US 9,181,147 B2
(45) Date of Patent: *Nov. 10, 2015

(54) PROCESS FOR THE PRODUCTION OF XYLENES AND LIGHT OLEFINS

(75) Inventors: Larry L. Iaccino, Seabrook, TX (US); S. Mark Davis, Humble, TX (US); John D. Y. Ou, Houston, TX (US); Xiaobo Zheng, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/465,733

(22) Filed: May 7, 2012

(65) Prior Publication Data

US 2013/0296622 A1 Nov. 7, 2013

(51) Int. Cl.
| | |
|---|---|
| *C07C 1/24* | (2006.01) |
| *C07C 2/86* | (2006.01) |
| *C10G 29/20* | (2006.01) |
| *C10G 35/00* | (2006.01) |
| *C10G 57/00* | (2006.01) |
| *C10G 9/00* | (2006.01) |
| *C10G 9/36* | (2006.01) |
| *C10G 11/00* | (2006.01) |

(52) U.S. Cl.
CPC ............... *C07C 2/864* (2013.01); *C10G 9/005* (2013.01); *C10G 9/36* (2013.01); *C10G 11/00* (2013.01); *C10G 29/205* (2013.01); *C10G 35/00* (2013.01); *C10G 57/005* (2013.01); *C10G 2300/1092* (2013.01); *C10G 2300/1096* (2013.01); *C10G 2400/30* (2013.01)

(58) Field of Classification Search
USPC ......... 585/708, 752, 709, 710, 717, 648, 653, 585/470, 310, 319, 323, 483, 400
See application file for complete search history.

(56) References Cited

U.S. PATENT DOCUMENTS

| | | | |
|---|---|---|---|
| 2,415,272 A | 2/1947 | Benedict et al. | |
| 3,409,540 A | 11/1968 | Gould et al. | |
| 3,862,898 A | 1/1975 | Boyd et al. | |
| 3,894,934 A * | 7/1975 | Owen et al. | 208/78 |
| 4,053,388 A | 10/1977 | Bailey | |
| 4,058,450 A | 11/1977 | LePage et al. | |
| 4,058,454 A | 11/1977 | Asselin | |
| 4,078,990 A | 3/1978 | Brennan et al. | |
| 4,257,871 A | 3/1981 | Wernicke et al. | |
| 4,980,053 A | 12/1990 | Li et al. | |
| 5,043,502 A | 8/1991 | Martindale et al. | |
| 5,232,675 A | 8/1993 | Shu et al. | |
| 5,326,465 A | 7/1994 | Yongqing et al. | |
| 5,358,918 A | 10/1994 | Yukang et al. | |
| 5,380,690 A | 1/1995 | Zhicheng et al. | |
| 5,932,777 A | 8/1999 | Sughrue et al. | |
| 6,077,984 A | 6/2000 | Drake et al. | |
| 6,080,698 A | 6/2000 | Zhang et al. | |
| 6,114,592 A | 9/2000 | Gajda et al. | |
| 6,153,089 A | 11/2000 | Das et al. | |
| 6,210,562 B1 | 4/2001 | Xie et al. | |
| 6,211,104 B1 | 4/2001 | Shi et al. | |
| 6,342,153 B1 | 1/2002 | Guan et al. | |
| 6,420,621 B2 | 7/2002 | Sha et al. | |
| 6,423,879 B1 | 7/2002 | Brown et al. | |
| 6,504,073 B1 | 1/2003 | Ushio et al. | |
| 6,635,792 B2 | 10/2003 | Choi et al. | |
| 6,740,788 B1 | 5/2004 | Maher et al. | |
| 7,119,239 B2 | 10/2006 | Johnson et al. | |
| 7,153,478 B2 | 12/2006 | Xu et al. | |
| 7,176,339 B2 | 2/2007 | Iaccino et al. | |
| 7,179,434 B1 | 2/2007 | Maher et al. | |
| 7,288,687 B1 | 10/2007 | Frey et al. | |
| 7,297,831 B2 | 11/2007 | Lee et al. | |
| 7,301,063 B2 | 11/2007 | Choi et al. | |
| 7,396,967 B2 * | 7/2008 | Iaccino et al. | 585/323 |
| 7,553,791 B2 | 6/2009 | McMinn et al. | |
| 7,563,358 B2 | 7/2009 | Stavens et al. | |
| 7,578,929 B2 | 8/2009 | Stell et al. | |

(Continued)

FOREIGN PATENT DOCUMENTS

| | | |
|---|---|---|
| AU | 776 247 | 9/2004 |
| EP | 0 136 072 | 4/1985 |
| EP | 0136072 | 4/1985 |
| EP | 1 068 166 | 3/2004 |
| EP | 1068166 | 3/2004 |
| KR | 10-0632571 | 10/2006 |
| WO | WO 97/45387 | 12/1997 |
| WO | WO 01/79383 | 10/2001 |
| WO | 02/44306 | 6/2002 |

(Continued)

OTHER PUBLICATIONS

U.S. Appl. No. 61/421,917, filed Dec. 10, 2010, Ellrich et al.

(Continued)

*Primary Examiner* — In Suk Bullock
*Assistant Examiner* — Sharon Pregler

(57) ABSTRACT

In a hydrocarbon upgrading process, a hydrocarbon feed is treated in at least one of a steam cracker, catalytic cracker, coker, hydrocracker, and reformer under suitable conditions to produce a first stream comprising olefinic and aromatic hydrocarbons. A second stream composed mainly of $C_4+$ olefinic and aromatic hydrocarbons is recovered from the first stream and is fed together with a methylating agent to a reaction zone containing a catalyst under reaction conditions including a temperature of about 450° C. to about 700° C., such that aromatics components in the second stream undergo dealkylation, transalkylation and/or methylation and aliphatic components undergo cracking and aromatization to produce a third stream having an increased xylene content compared with said second stream and a $C_3-$ olefin by-product. The $C_3-$ olefin by-product is recovered and para-xylene is removed from at least part of said third stream.

25 Claims, 1 Drawing Sheet

(56) References Cited

U.S. PATENT DOCUMENTS

| | | |
|---|---|---|
| 7,601,311 B2 | 10/2009 | Casey et al. |
| 7,629,498 B2 | 12/2009 | Brown et al. |
| 7,727,490 B2 | 6/2010 | Zhou |
| 7,923,399 B2 | 4/2011 | Long et al. |
| 7,939,702 B2 | 5/2011 | Choi et al. |
| 7,972,498 B2 | 7/2011 | Buchanan et al. |
| 8,183,424 B2 | 5/2012 | Levin et al. |
| 2001/0053868 A1 | 12/2001 | Chester et al. |
| 2002/0092797 A1 | 7/2002 | Choi et al. |
| 2003/0105372 A1 | 6/2003 | Feng et al. |
| 2003/0116471 A1 | 6/2003 | Zhang et al. |
| 2004/0015027 A1 | 1/2004 | Iaccino et al. |
| 2004/0049093 A1 | 3/2004 | Cheung et al. |
| 2005/0020867 A1 | 1/2005 | Xie et al. |
| 2005/0209495 A1 | 9/2005 | McCoy et al. |
| 2006/0194996 A1 | 8/2006 | Umansky et al. |
| 2008/0051615 A1 | 2/2008 | Stavens et al. |
| 2008/0249345 A1 | 10/2008 | Kin et al. |
| 2009/0000988 A1 | 1/2009 | Brown et al. |
| 2010/0040517 A1 | 2/2010 | Brown et al. |
| 2012/0149958 A1 | 6/2012 | Ellrich et al. |

FOREIGN PATENT DOCUMENTS

| | | |
|---|---|---|
| WO | WO 2004/005432 | 1/2004 |
| WO | WO 2006/068800 | 6/2006 |
| WO | 2007-108573 | 9/2007 |
| WO | WO 2007/108573 | 9/2007 |
| WO | WO 2010/138504 | 12/2010 |
| WO | WO 2012/015541 | 2/2012 |

OTHER PUBLICATIONS

Baillie et al., *"FCC Catalysts: Now Rare Earth Free,"* Hydrocarbon Engineering, Mar. 2011, vol. 16, No. 3, pp. 33-36.

* cited by examiner

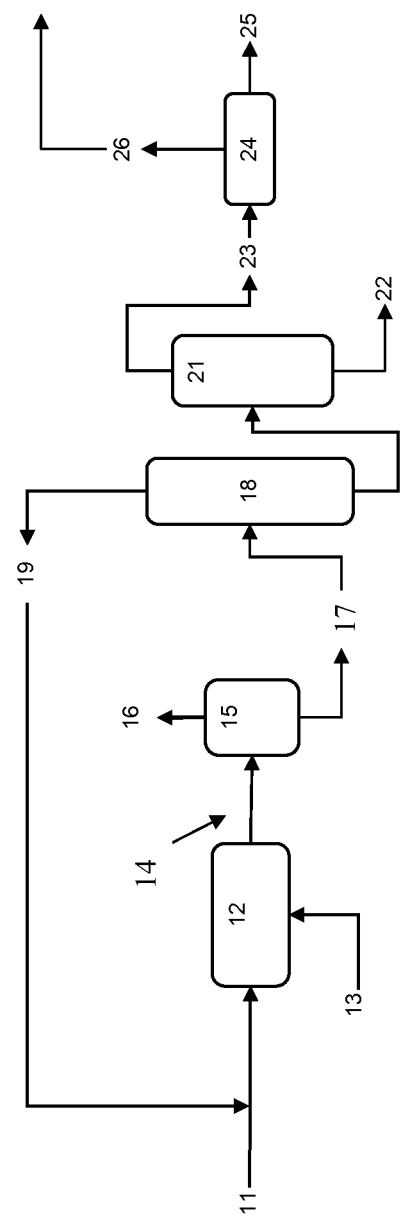

US 9,181,147 B2

PROCESS FOR THE PRODUCTION OF XYLENES AND LIGHT OLEFINS

STATEMENT OF RELATED CASES

This application is related to U.S. Ser. No. 13/303,855, filed Nov. 23, 2011 which claims the benefit of and priority to U.S. Ser. No. 61/421,917 filed Dec. 10, 2010.

FIELD OF THE INVENTION

This invention relates to a process for the production of xylenes and light ($C_4$–) olefins from diverse olefinic feedstocks.

BACKGROUND OF THE INVENTION

Xylene isomers find wide and varied application. They are especially valuable as intermediates in chemical processes. By way of example, para-xylene (PX) is a feedstock for terephthalic acid, which finds use in the manufacture of polyester fibers and films, meta-xylene (MX) is used in the manufacture of dyes, and ortho-xylene (OX) is used as a feedstock for phthalic anhydride, which finds use in the manufacture of plasticizers. PX is currently the most valuable of the xylene isomers and, although research related to obtaining (e.g., producing or purifying) PX is too voluminous to mention, there is still intensive research in the area.

There are many possible feeds currently used to obtain PX. The majority of para-xylene produced today comes from catalytic reforming, which involves dehydrogenation and dehydrocyclization of naphtha feedstocks. The effluent of the reforming process, known as reformate, is rich in aromatics, particularly benzene, toluene, and mixed xylenes (BTX), and is used as feedstock to aromatics plants. Processes exist to increase the yield of para-xylene over the equilibrium mixture in the reformate, including selective toluene disproportionation and selective methylation of benzene and/or toluene with methanol.

Recently, significant research has focused on finding alternative sources and methods for producing BTX and particularly para-xylene. For example, although steam cracking, or pyrolysis, is the preferred method of producing light olefins (ethylene, propylene, and butenes) from heavier hydrocarbon feedstocks, the process also generates a by-product termed pyrolysis gasoline, steam cracked naphtha (SCN) or pygas. Pygas is a complex mixture of $C_6$ to $C_{10}$+ hydrocarbons that is rich in aromatics, particularly benzene and toluene, but also contains $C_8$, $C_9$, and $C_{10}$+ aromatics. Similarly, catalytic cracking, particularly fluid catalytic cracking (FCC), in addition to producing fuels and light olefins, generates a $C_6$ to $C_{10}$+ aromatic rich stream which is similar to pygas and is generally known as cat naphtha. These processes also produce $C_4$ and $C_5$ olefinic streams (containing di-olefins and acetylenes) which have some utility but tend to be of lower value than aromatic products and lighter olefins (ethylene and propylene). There is, therefore, significant interest in developing methods of upgrading alternate feed sources, such as pygas and cat naphtha, to increase the yield of ethylene, propylene, BTX; and preferably para-xylene and propylene. There are some processes proposed to upgrade these streams to produce BTX but they consume expensive $H_2$ and co-produce lower value light saturates rather than higher value light olefins.

For example, U.S. Pat. No. 6,635,792 discloses a process for producing BTX and liquefied petroleum gas (LPG) from a hydrocarbon feedstock having boiling points of 30° C. to 250° C., such as reformate and pyrolysis gasoline. In the process, aromatic components in the hydrocarbon feedstock are converted to BTX-enriched components in the liquid phase through hydrodealkylation and/or transalkylation, and non-aromatic components are converted to LPG-enriched gaseous materials through hydrocracking. The process employs a catalyst comprising platinum/tin or platinum/lead on mordenite, zeolite beta, or ZSM-5. U.S. Pat. Nos. 7,297,831 and 7,301,063 disclose similar processes.

U.S. Pat. No. 7,176,339 discloses a process for producing xylenes from reformate, which process comprises: (a) providing a reformate containing hydrogen, $C_1$ to $C_5$ hydrocarbons, $C_6$ to $C_7$ hydrocarbons comprising benzene, toluene or mixtures thereof, and $C_8$+ hydrocarbons; (b) removing at least a portion of said hydrogen from said reformate to produce a product containing $C_6$ to $C_7$ hydrocarbons comprising benzene, toluene, or mixtures thereof, and $C_8$+ hydrocarbons; and (c) methylating at least a portion of the benzene, toluene, or mixtures thereof present in said product with a methylating agent under vapor phase conditions and in the presence of a catalyst effective for the methylation to produce a resulting product having a higher para-xylene content than the reformate, wherein the catalyst comprises a zeolite-bound-zeolite catalyst and/or a selectivated zeolite and the zeolite comprises ZSM-5. A similar process is disclosed in U.S. Pat. No. 7,629,498.

U.S. Pat. No. 7,563,358 discloses process for producing BTX-enriched product from a hydrocarbon feed comprising: (a) $C_6$+ non-aromatic cyclic hydrocarbons; (b) $C_8$+ single-ring aromatic hydrocarbons having at least one alkyl group containing two or more carbon atoms; and (c) $C_9$+ single-ring aromatic hydrocarbons having at least three methyl groups, by contacting the feed in the presence of hydrogen with a catalyst comprising at least one Group VIII metal and a large or intermediate pore molecular sieve having an alpha value, before incorporation of the Group VIII metal, from about 2 to less than 100 under conditions sufficient for (i) forming aromatic hydrocarbons from $C_6$+ non-aromatic cyclic hydrocarbons; (ii) dealkylating $C_8$+ single-ring aromatic hydrocarbons having at least one alkyl group containing two or more carbon atoms; (iii) transalkylating $C_9$+ single-ring aromatic hydrocarbons having at least three methyl groups; and (iv) disproportionating toluene, to produce a product containing an increased amount of BTX compared to the feed. A preferred hydrocarbon feed is steam cracked naphtha.

In U.S. Applications U.S. Ser. No. 61/421,917 filed Dec. 10, 2010 and U.S. Ser. No. 13/303,855, filed Nov. 23, 2011, we have described a hydrocarbon upgrading process comprising (a) treating a first hydrocarbon stream in at least one of a steam cracker, catalytic cracker, coker, hydrocracker, reformer, and the like, under suitable conditions to produce a second stream comprising $C_6$ to $C_{10}$+ aromatic hydrocarbons; (b) dealkylating and/or transalkylating and/or cracking (D/T/C) the second stream by contact with a suitable catalyst under suitable reaction conditions to produce a third stream having an increased benzene and/or toluene content compared with the second stream and a light paraffin by-product; and (c) methylating at least a portion of the third stream with a methylating agent to selectively produce para-xylene. By integrating different upgrading steps, this process offers significant advantages in terms of higher petrochemical yields and lower energy consumption as compared with existing processes for enriching the BTX content of hydrocarbon streams.

Further investigation into the process described in U.S. Ser. No. 61/421,917 and U.S. Ser. No. 13/303,855 has, however, now shown that, by feeding the methylating agent to the D/T/C step under conditions that favor the production of light olefins as well as benzene and/or toluene, the feedstock window (broader carbon number) of the process can be increased, feed preparation can be simplified, and hydrogen usage can be reduced. In addition, the process generates additional aromatic rings and co-produces light ($C_3-$) olefins, which are in high demand in the chemical industry, rather than lower value products, such as LPG. Further, the need for a separate methylating step can be avoided, thereby reducing capital cost.

SUMMARY OF THE INVENTION

Accordingly, the invention resides in one aspect in a hydrocarbon upgrading process comprising:

(a) treating a hydrocarbon feed in at least one of a steam cracker, catalytic cracker, coker, hydrocracker, and reformer under suitable conditions to produce a first stream comprising olefinic and aromatic hydrocarbons;

(b) recovering from said first stream a second stream composed mainly of $C_4+$ olefinic and aromatic hydrocarbons;

(c) feeding said second stream and a methylating agent to a reaction zone containing a catalyst under reaction conditions including a temperature of about 450° C. to about 700° C., such that aromatics components in the second stream undergo dealkylation, transalkylation and/or methylation, and aliphatic components undergo cracking and aromatization to produce a third stream having an increased xylene content compared with said second stream and a $C_3-$ olefin by-product;

(d) recovering the $C_3-$ olefin by-product; and (e) recovering at least para-xylene from at least part of said third stream.

Conveniently, the hydrocarbon feed is selected from natural gas liquids, natural gas condensate, naphtha, distillate, gas oils, crude oil, and/or resids.

Generally, the methylating agent of (c) comprises methanol.

In one embodiment, the second stream is composed mainly of $C_4$ to $C_{12}+$ olefinic and aromatic hydrocarbons and the catalyst in (c) comprises a molecular sieve having a Constraint Index less than 3, such as zeolite Y or zeolite beta, and, optimally, also contains a molecular sieve having a Constraint Index of about 3 to about 12, such as an MFI zeolite, especially an MFI zeolite that has been phosphorus stabilized.

In another embodiment, the second stream is composed mainly of $C_4$ to $C_8$ olefinic and aromatic hydrocarbons and the catalyst in (c) comprises a molecular sieve having a Constraint Index of about 3 to about 12, such as a mordenite framework inverted (MFI) zeolite, especially an MFI zeolite that has been phosphorus stabilized and/or selectivated so as to have an equilibrium sorption capacity for xylene of at least 1 gram per 100 grams of zeolite measured at 120° C. and a xylene pressure of 4.5±0.8 mm of mercury and an ortho-xylene sorption time for 30% of its equilibrium ortho-xylene sorption capacity of greater than 1200 minutes. Preferably, a selectivated catalyst is a catalyst that has had diffusion and/or external surface activity modified so as to produce paraxylene at above equilibrium concentrations.

Conveniently, the reaction conditions include a temperature of about 550° C. to about 620° C. and a pressure of about 70 kPaa to about 700 kPaa.

Conveniently, (c) is carried out in a moving bed reactor, preferably a fluid bed reactor, and part of the catalyst is removed from the reactor and circulated to an oxidative regenerator. Generally, additional fuel is added to the regenerator to heat the catalyst to provide a portion of the heat of reaction for step (c).

Conveniently, the process further comprises one or more of:

(i) removing $C_4+$ olefins and saturated aliphatics from the third stream and recycling said $C_4+$ olefins and saturated aliphatics to (c);

(ii) removing benzene and/or toluene from the third stream and recycling said benzene and/or toluene to (c); and (iii) recovering benzene as a product from the third stream.

In one embodiment, the process further comprises removing a $C_8$ stream from the third stream and recovering para-xylene from said $C_8$ stream in (e). Typically, recovery of para-xylene from the $C_8$ stream is affected in a crystallization and/or adsorption unit and produces a para-xylene depleted stream. The para-xylene depleted stream can then be isomerized to equilibrium and the equilibrated stream recycled to the crystallization and/or adsorption unit to recover further para-xylene therefrom.

BRIEF DESCRIPTION OF THE DRAWINGS

FIG. 1 is a schematic drawing of a hydrocarbon upgrading process according to a first embodiment of the present invention.

DETAILED DESCRIPTION OF THE EMBODIMENTS

As used herein, the term "$C_n$" hydrocarbon wherein n is a positive integer, e.g., 1, 2, 3, 4, 5, 6, 7, 8, 9, 10, 11, 12, as used herein, means a hydrocarbon having n number of carbon atom(s) per molecule. The term "$C_n+$" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n-$" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

As used herein "resid" refers to the complex mixture of heavy petroleum compounds otherwise known in the art as residuum or residual. Atmospheric resid is the bottoms product produced in atmospheric distillation where the endpoint of the heaviest distilled product is nominally 650° F. (343° C.), and is referred to as 650° F.$^+$ (343° C.) resid. Vacuum resid is the bottoms product from a column under vacuum where the heaviest distilled product is nominally 1050° F. (566° C.), and is referred to as 1050° F.$^+$ (566° C.$^+$) resid. (The term "nominally" means here that reasonable experts may disagree on the exact cut point for these terms, but probably by no more than +/−50° F. or at most +/−100° F.) The term "resid" as used herein means the 650° F.$^+$ (343° C.$^+$) resid and 1050° F.$^+$ (566° C.$^+$) resid unless otherwise specified (note that 650° F.$^+$ resid comprises 1050° F.$^+$ resid).

Described herein is a hydrocarbon upgrading process, in which a hydrocarbon feed is treated in at least one of a steam cracker, catalytic cracker, coker, hydrocracker, and reformer under suitable conditions to produce a first stream enriched in olefinic and/or aromatic hydrocarbons. A second stream composed mainly of $C_4+$ olefinic and aromatic hydrocarbons is separated from the first stream and is fed together with a methylating agent, such as methanol, to a catalytic reactor where the components of the stream undergo dealkylation, transalkylation, cracking, aromatization, and methylation (DTCAM) to produce a third stream having an increased xylene content as compared with said second stream and a $C_3-$ olefin by-product. The $C_3-$ olefin by-product is separated from the third stream and recovered for use as a chemical feedstock, whereafter the third stream is passed to a paraxylene recovery unit where at least the para-xylene isomer is recovered from the third stream.

Hydrocarbon Feedstock

Any hydrocarbon composition conventionally fed to a steam cracker, catalytic cracker, coker, hydrocracker, or reformer can be used as the hydrocarbon feed in the present process. Thus, for example, the hydrocarbon feed can comprise a natural gas liquid or condensate, naphtha, gas oil, or any distillate fraction of whole crude oil, including, in some cases, the residual fraction remaining after an atmospheric or vacuum distillation process (i.e. resid).

Treating the hydrocarbon feed in the steam cracker, catalytic cracker, coker, hydrocracker, or reformer produces a first hydrocarbon stream having a broad spectrum of olefinic and aromatic hydrocarbons depending on the initial composition of the hydrocarbon feed and also on the unit used to process the feed. The first hydrocarbon stream is then subjected to one or more separation operations to recover $C_3-$ olefins, such as ethylene and propylene, fuel gas, and certain heavier hydrocarbons and leave a second hydrocarbon stream composed mainly $C_4+$ olefinic and aromatic hydrocarbons. Again, the precise composition of the second hydrocarbon stream will depend on the initial composition of the hydrocarbon feed and on the unit used to process the feed. In addition, the composition of the second hydrocarbon stream is adjusted in accordance with the intended operation of the downstream DTCAM reactor. Thus, where the DTCAM reactor is intended to produce a high proportion of para-xylene, the second hydrocarbon stream preferably contains mostly $C_4$ to $C_8$ olefinic and aromatic hydrocarbons. Alternatively, where the DTCAM reactor is intended to produce a mixed xylene product, the second hydrocarbon stream preferably contains mostly $C_4$ to $C_{12}$ olefinic and aromatic hydrocarbons. In fact, in the latter case, depending on the operating targets and efficiency of the fractionation steps used to remove the unwanted components, the second hydrocarbon stream may contain quantities (generally less than 20 wt %) of $C_3-$ and $C_{12}+$ hydrocarbons.

In one preferred embodiment, in which a steam cracker is employed as the process unit, the second hydrocarbon stream is a pyrolysis gasoline containing from about 15 wt % to about 65 wt % benzene, from about 5 wt % to about 35 wt % toluene, from about 1 wt % to about 15 wt % of $C_8+$ aromatic compounds and up to 50 wt %, typically about 1 wt % to about 15 wt %, non-aromatics, the exact composition depending on the composition of feedstock to the steam cracker, the intensity of the pyrolysis reaction, and the separation and processing scheme for the pygas stream.

In another preferred embodiment, in which a steam cracker is employed as the process unit, the second hydrocarbon stream is a $C_4$ to $C_{10}$ containing stream which, in one example, has the composition given in Table 1 below:

TABLE 1

| Species | Wt % |
|---|---|
| C4 diolefins | 10.3% |
| C4 olefins | 11.9% |
| C4 saturates | 1.1% |
| C5 cyclo-diolefins | 3.8% |
| C5 diolefins | 4.3% |
| C5 cyclo-olefins | 0.8% |
| C5 cyclo sat's | 0.0% |
| C5 olefins (other) | 2.6% |
| C5 saturates (other) | 1.0% |
| C6 cyclodiolefins | 1.6% |
| C6 cyclo-olefins | 0.3% |
| C6 cyclo-olefins | 2.0% |

TABLE 1-continued

| Species | Wt % |
|---|---|
| C6 olefins (other) | 0.9% |
| C6 saturates (other) | 0.8% |
| Benzene | 10.7% |
| C7 olefins | 2.4% |
| C7 saturates | 1.6% |
| Toluene | 7.6% |
| C8 olefins | 1.1% |
| C8 saturates | 0.9% |
| Ethylbenzene | 3.2% |
| Xylenes | 3.6% |
| Indanes | 7.8% |
| Isopropylbenzenes | 0.1% |
| Propylbenzenes | 0.3% |
| Trimethylbenzenes | 1.8% |
| Methylethylbenzenes | 3.1% |
| Trimethylcyclohexanes | 0.0% |
| Propylcyclohexanes | 0.1% |
| Butylcyclopentane | 7.3% |
| Nonane | 0.1% |
| Methyloctanes | 0.0% |
| Dimethylheptanes | 0.0% |
| Trimethylhexanes | 0.0% |
| Naphthalene | 2.1% |
| Methylindanes | 1.8% |
| Dimethylethylbenzenes | 1.5% |
| Methylpropylbenzenes | 0.1% |
| Butylbenzenes | 0.2% |
| Decane | 0.0% |
| Methylnonanes | 0.0% |
| Dimethyloctanes | 0.0% |
| Dicyclopentanes | 1.1% |
| Total | 100.0% |

Generally, as the intensity of the pyrolysis reaction increases, which can be noted by the rising outlet temperature of the reactor or by the changing of the ratio of two products, such as propylene and methane, more aromatics will be present in the effluent. Similarly, as weight of the feedstock to the pyrolysis furnace increases, the yield of aromatics in the pygas will also increase. Naphthas and gas oils are conventional feedstocks to steam crackers, including virgin and hydrotreated streams. Resid-containing feeds (typically containing a lesser portion of 1050° F.+ resid, preferably 20 wt % or less 1050° F.+ resid, based upon the weight of the feed, preferably 10 wt % or less) can be processed by first passing through the convection section of the steam cracking furnace, then passing to a vapor/liquid separating drum, which can optionally be integrated with the pyrolysis furnace, to drop out the heaviest fraction.

Dealkylation, Transalkylation, Cracking, Aromatization, and Methylation

The entire $C_4+$ second hydrocarbon stream is normally supplied to the DTCAM reactor, along with a methylating agent, such as methanol, where the second stream and the methanol are contacted with a catalyst in the absence of added hydrogen under reaction conditions including a temperature of about 450° C. to about 700° C., such as about 550° C. to about 620° C., and a pressure of about 70 kPaa to 700 kPaa, such as 200 kPaa to 350 kPaa. Steam may also be fed to the reactor, for example, to lower the partial pressure of the hydrocarbon feed.

The catalyst is normally contained in a moving bed, such as a fluid bed, and typically comprises one or more molecular sieves, especially aluminosilicate zeolites. The particular molecular sieve(s) employed will depend on the desired xylene composition of the DTCAM product. Thus, where the desired $C_8$ component of the product is mixed xylenes and the feed comprises mostly $C_4$ to $C_{12}$ olefinic and aromatic hydrocarbons, the catalyst preferably comprises a large pore molecular sieve. Large pore molecular sieves are generally defined as those having a pore size in excess of 7 Angstroms (e.g. greater than 7 Angstroms). Another common definition for large pore molecular sieves involves the Constraint Index test, which is described in U.S. Pat. No. 4,016,218, which is incorporated herein by reference. In this case, large pore molecular sieves have a Constraint Index less than 3, as measured on the zeolite alone without any treatment to adjust the diffusivity of the catalyst. Particular examples of suitable large pore zeolites include zeolite Y, ultra stable Y-type zeolites (USY), rare earth exchanged Y-type zeolites (REY), rare earth exchanged ultra stable Y-type zeolites (REUSY), rare earth free Z-21 and Z-22, MCM-22 and zeolite beta. Optionally, the catalyst employed with $C_4$ to $C_{12}$ olefinic and aromatic hydrocarbon comprises a medium pore zeolite (as defined below), especially ZSM-5, in combination with a large pore molecular sieve.

Alternatively, where the desired $C_8$ component of the product comprises para-xylene in excess of equilibrium concentration and the feed comprises mostly $C_4$ to $C_8$ olefinic and aromatic hydrocarbons, the catalyst preferably comprises a medium pore zeolite. Medium pore zeolites are generally defined as those having a pore size of about 5 to 7 Angstroms, such that the zeolite freely sorbs molecules such as n-hexane, 3-methylpentane, benzene, and p-xylene. Another common definition for medium pore zeolites involves the Constraint Index test in which case, medium pore zeolites have a Constraint Index of 3 to about 12, as measured on the zeolite alone without any treatment to adjust the diffusivity of the catalyst. Particular examples of suitable medium pore zeolites include ZSM-5, ZSM-11, ZSM-12, ZSM-22, ZSM-23, ZSM-35, and ZSM-48, with MFI type zeolites, such as ZSM-5 and ZSM-11, being particularly preferred. Little or no large pore zeolitic component, such as zeolite Y, is normally included in the catalyst in this embodiment since such a component would tend to isomerize para-xylene, preferably the large pore zeolitic component is present at less than 0.5 wt %, preferably at 0 wt %, based upon the weight of the zeolite.

In addition to the zeolitic components, the DTCAM catalyst normally comprises a binder or matrix material that is resistant to the temperatures and other conditions employed in the reactor. Such materials include active and inactive materials and synthetic or naturally occurring zeolites, as well as inorganic materials such as clays, silica, and/or metal oxides such as alumina. The inorganic material may be either naturally occurring, or in the form of gelatinous precipitates or gels, including mixtures of silica and metal oxides. Use of a binder or matrix material which itself is catalytically active, may change the conversion and/or selectivity of the catalyst composition. Inactive materials suitably serve as diluents to control the rate of reaction. These catalytically active or inactive materials may include, for example, naturally occurring clays, e.g., bentonite and kaolin, to improve the crush strength of the catalyst composition under commercial operating conditions. Other suitable matrix or binder materials include inorganic oxides selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Typically the catalyst contains a binder or matrix material in an amount ranging from 10 wt % to 95 wt % of the total catalyst.

Generally, the catalyst employed in the DTCAM reactor is phosphorus stabilized, which is conveniently achieved by impregnating the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 wt % and about 30 wt %. Suitable phosphorus compounds include, but are not limited to, phosphonic, phosphinous, phosphorus, and phosphoric acids, salts and esters of such acids and phosphorus halides. After contacting with one or more phosphorus-containing compounds, the catalyst is dried and the calcined in an inert atmosphere or in the presence of oxygen, for example, in air, at a temperature of about 150° C. to 750° C., preferably about 300° C. to 500° C., for at least 1 hour, preferably 3 to 5 hours.

In one embodiment, where a high para-xylene content product is desired, the DTCAM catalyst is selectivated so as to have an equilibrium sorption capacity for xylene of at least 1 gram per 100 grams of zeolite measured at 120° C., a xylene pressure of 4.5±0.8 mm of mercury, and an ortho-xylene sorption time for 30 percent of its equilibrium ortho-xylene sorption capacity of greater than 1200 minutes, e.g., greater than about 1500, e.g., greater than about 2000 minutes, e.g., greater than about 2500 minutes. For materials with very long ortho-xylene sorption times, it may be more convenient to determine the sorption time for a lower extent of sorption, such as 5%, 10%, or 20% of capacity, and then to estimate the 30% sorption time by applying the following multiplication factors, F:

| Percent sorption capacity | Factor, F, to estimate 30% sorption time $t_{0.3}$ |
|---|---|
| 5 | 36 |
| 10 | 9 |
| 20 | 2.25 |

Alternatively, $t_{0.3}$ may be calculated for other sorption times less than 30% of xylene capacity using the following relationship:

$$t_{0.3} = (0.3/0.x)^2 (t_{0.x})$$

where:

$t_{0.3}$ is the sorption time for 30% of total xylene capacity;

$t_{0.x}$ is the sorption time for x % of total xylene capacity; and 0.x is the fractional amount of ortho-xylene sorption to total xylene capacity.

To provide the zeolite catalyst with the required ortho-xylene sorption properties, the zeolite is selectivated by treatment with aluminum phosphate and/or by multiple organosilicon compound impregnation/calcination steps.

Alternatively, where the catalyst employed is subjected to multiple stages of silicon selectivation each selectivation stage conveniently involves impregnating the catalyst with a silicon compound, normally an organosilicon compound, in a carrier liquid, followed by one or more calcination steps to remove the carrier liquid and convert the organosilicon compound to silica.

Useful selectivating agents include siloxanes which can be characterized by the general formula:

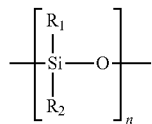

where $R_1$ and $R_2$ are, independently, hydrogen, halogen, hydroxyl, alkyl, halogenated alkyl, aryl, halogenated aryl, aralkyl, halogenated aralkyl, alkaryl, or halogenated alkaryl. The hydrocarbon substituents of $R_1$ and $R_2$ generally contain from 1 to 10 carbon atoms, preferably methyl, ethyl, or phenyl groups. "n" is an integer of at least 2 and generally in the range of 3 to 1000. The weight average molecular weight of the silicone compound employed is generally between about 80 and about 20,000 g/mol and preferably within the approximate range of 150 to 10,000 g/mol. Representative silicone compounds include dimethyl silicone, diethyl silicone, phenylmethyl silicone, methylhydrogen-silicone, ethylhydrogen silicone, phenylhydrogen silicone, methylethyl silicone, phenylethyl silicone, diphenyl silicone, methyltrifluoropropyl silicone, ethyltri-fluoropropyl silicone, polydimethyl silicone, tetrachloro-phenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclo-tetrasiloxane, hexaphenyl cyclotrisiloxane and octaphenyl cyclotetrasiloxane. Mixtures of these compounds may also be used, as may silicones with other functional groups.

Preferably, the kinetic diameter of the para-selectivating agent is larger than the zeolite pore diameter, in order to avoid entry of the selectivating agent into the pore and any concomitant reduction in the internal activity of the catalyst. Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich., USA.

Examples of suitable organic carriers for the selectivating silicon compound include hydrocarbons such as linear, branched, and cyclic alkanes having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, may also be employed as carriers. Particular low volatility hydrocarbon carriers of selectivating agents are decane and dodecane. Generally, the DTCAM catalyst is substantially free of hydrogenation metal (e.g. preferably contains less than 1,000 ppm by weight of hydrogenation metal) but may in some cases contain up to 10 ppm by weight of platinum as a CO combustion promoter.

Under the conditions specified above, the DTCAM catalyst is effective to dealkylate $C_8+$ single-ring aromatic hydrocarbons having at least one alkyl group containing two or more carbon atoms in the second hydrocarbon stream. Thus, exemplary reactions are cracking of ethylbenzene and cumene to benzene and ethylene and propylene, respectively. Other reactions include cracking and aromatization of aliphatic hydrocarbons in the feed to produce lower olefins and additional aromatic compounds.

In addition, in view of the methylating agent added with the $C_4$ to $C_{12}$ hydrocarbon feed to the DTCAM reactor, the reactions between the components of the hydrocarbon feed are accompanied by methylation of the aromatic species, especially benzene and toluene, present in feed and produced by the other reactions in the DTCAM reactor. One product of these reactions is xylene. Moreover, because of the shape selectivity of the DTCAM catalyst, such reactions tend to favor production of the para-isomer.

Apart from the desired reactions discussed above, the DTCAM catalyst effects non-selective conversion of the feed to coke which deposits on the catalyst causing its deactivation. Thus, part of the catalyst is continuously or intermittently removed from the reactor and circulated to an oxidative regenerator, where coke is burnt from the catalyst. Additional fuel may be added to the regenerator to heat the catalyst to the required regeneration temperature and to provide a portion of the heat of reaction required for the DTCAM reactions.

Treatment of DTCA Product

The effluent from the DTCAM reactor is a third hydrocarbon stream having an increased xylene content as compared with the second hydrocarbon stream and a $C_3-$ olefin byproduct. The $C_3-$ olefins are recovered from the effluent for use as a chemical feedstock and the remainder of the effluent is fed to a distillation system where at least a $C_7-$ fraction and a $C_8$ fraction are separated from the third hydrocarbon stream. The remainder of the third hydrocarbon stream, which is composed mainly of $C_9+$ hydrocarbons, can be recovered for use as fuel oil, among other things.

The entire $C_7-$ fraction of the third hydrocarbon stream, composed mainly of $C_4+$ to $C_7$ olefins, saturated aliphatics and aromatics can be recycled back to DTCAM reactor or a benzene-rich and/or a toluene-rich fraction can be recovered from the $C_7-$ fraction before the remainder of the fraction is recycled to the DTCAM reactor. Alternatively, the distillation of the third hydrocarbon stream can be arranged to separate benzene and/or toluene as the $C_7-$ fraction, with the benzene and/or toluene then being recycled to the DTCAM reactor.

The $C_8$ fraction separated from the third hydrocarbon stream is fed to a para-xylene recovery unit where para-xylene is recovered therefrom, normally by either crystallization and/or adsorption, to leave a para-xylene depleted stream. The para-xylene depleted stream can then be recycled to the DTCAM reactor but more preferably is fed to a xylene isomerization unit where the para-xylene depleted stream is isomerized to equilibrium. The equilibrated stream can then be recycled to the para-xylene recovery unit to recover additional para-xylene therefrom.

The invention will now be more particularly described with reference to the accompanying drawing and the following non-limiting Examples.

Referring initially to FIG. 1, a raw $C_4+$ aliphatic and aromatic hydrocarbon product from a steam cracker (not shown) is fed by line 11 to a DTCAM reactor 12 which also receives a methanol feed from line 13. The gaseous effluent from the reactor 12 is fed by line 14 to a cooler 15, where the $C_4+$ components condense and the $C_3-$ components are recovered through line 16. The condensed $C_4+$ components are fed by line 17 from the cooler 15 to a first distillation tower 18, where a $C_4$ to $C_7$ fraction is removed and recycled via overhead line 19 to the reactor 12. The remaining $C_8+$ fraction of the DTCAM effluent is fed to a second distillation tower 21, where the $C_9+$ hydrocarbons are removed via line 22 for use as fuel oil, while the $C_8$ fraction is fed by line 23 to a para-xylene recovery unit 24. Para-xylene is removed from the $C_8$ fraction in unit 24 and is recovered via line 25, whereas the remaining para-xylene depleted fraction is fed to a xylene isomerization unit (not shown) by line 26.

This invention further relates to:

1. A hydrocarbon upgrading process comprising:
   (a) treating a hydrocarbon feed in at least one of a steam cracker, catalytic cracker, coker, hydrocracker, and reformer under suitable conditions to produce a first stream comprising olefinic and aromatic hydrocarbons;
   (b) recovering from said first stream a second stream composed mainly of $C_4$+ olefinic and aromatic hydrocarbons;
   (c) feeding said second stream and a methylating agent to a reaction zone containing a catalyst under reaction conditions including a temperature of about 450° C. to about 700° C., such that aromatics components in the second stream undergo dealkylation, transalkylation and/or methylation and aliphatic components undergo cracking and aromatization to produce a third stream having an increased xylene content compared with said second stream and a $C_3$− olefin by-product;
   (d) recovering the $C_3$− olefin by-product; and
   (e) recovering at least para-xylene from at least part of said third stream.
2. The process of paragraph 1, wherein the hydrocarbon feed is selected from natural gas liquids, natural gas condensate, naphtha, distillate, gas oils, crude oil, and/or resids.
3. The process of paragraph 1 or 2, wherein the methylating agent in (c) comprises methanol.
4. The process of paragraph 1, 2 or 3, wherein the second stream is composed mainly of $C_4$ to $C_{12}$+ olefinic and aromatic hydrocarbons and the catalyst in (c) comprises a molecular sieve having a Constraint Index less than 3.
5. The process of paragraph 4, wherein the catalyst in (c) comprises zeolite Y or zeolite beta.
6. The process of paragraph 4, wherein the catalyst in (c) further comprises a molecular sieve having a Constraint Index of about 3 to about 12.
7. The process of paragraph 5, wherein the catalyst in (c) further comprises an MFI zeolite.
8. The process of any of paragraphs 1 to 7, wherein the second stream is composed mainly of $C_4$ to $C_8$ olefinic and aromatic hydrocarbons and the catalyst in (c) comprises a molecular sieve having a Constraint Index of about 3 to about 12.
9. The process of paragraph 8, wherein said catalyst in (c) comprises an MFI zeolite.
10. The process of paragraph 9, wherein said MFI zeolite is phosphorus stabilized.
11. The process of paragraph 10, wherein said MFI zeolite has been selectivated so as to have an equilibrium sorption capacity for xylene of at least 1 gram per 100 grams of zeolite measured at 120° C. and a xylene pressure of 4.5±0.8 mm of mercury and an ortho-xylene sorption time for 30% of its equilibrium ortho-xylene sorption capacity of greater than 1200 minutes.
12. The process of any of paragraphs 1 to 11, wherein said catalyst in (c) is substantially free of hydrogenation metal.
13. The process of any of paragraphs 1 to 12, wherein said reaction conditions in (c) include a temperature of about 550° C. to about 620° C.
14. The process of any of paragraphs 1 to 13, wherein said reaction conditions in (c) include a pressure of about 70 kPaa to about 700 kPaa.
15. The process of any of paragraphs 1 to 14, wherein (c) is carried out in a moving bed reactor.
16. The process of any of paragraphs 1 to 14, wherein (c) is carried out in a fluid bed reactor.
17. The process of paragraph 16, wherein part of the catalyst is removed from the reactor and circulated to an oxidative regenerator.
18. The process of paragraph 17, wherein additional fuel is added to the regenerator to heat the catalyst to provide a portion of the heat of reaction for step (c).
19. The process of any of paragraphs 1 to 18, further comprising removing $C_4$+ olefins and saturated aliphatics from the third stream and recycling said $C_4$+ olefins and saturated aliphatics to (c).
20. The process of any of paragraphs 1 to 19, further comprising removing benzene and/or toluene from the third stream and recycling said benzene and/or toluene to (c).
21. The process of any of paragraphs 1 to 20, further comprising recovering benzene from the third stream.
22. The process of any of paragraphs 1 to 21, further comprising removing a $C_8$ stream from the third stream and recovering para-xylene from said $C_8$ stream in (e).
23. The process of paragraph 22, wherein recovering para-xylene from said $C_8$ stream is affected in a crystallization and/or adsorption unit and also produces a para-xylene depleted stream.
24. The process of paragraph 23, wherein the para-xylene depleted stream is isomerized to equilibrium and the equilibrated stream is recycled to the crystallization and/or adsorption unit to recover para-xylene therefrom.

Example 1

This Example provides the estimated results of employing the process shown in FIG. 1 to upgrade 1831 kta of a $C_4$ to $C_8$ steam cracked feed having the composition shown in Table 2 below. 523 kta of methanol was supplied to the DTCAM reactor 12. The $C_3$− olefin by-product recovered via line 16 was composed of 384 kta of ethylene, 605 kta propylene, and 68 kta of saturates. The amount of para-xylene product recovered via line 25 was 916 kta. The amount of mixed-xylene byproduct recovered via line 26 was 266 kta.

TABLE 2

| Species | kta |
|---|---|
| C4 diolefins | 260 |
| C4 olefins | 302 |
| C4 saturates | 27 |
| C5 cyclo-diolefins | 96 |
| C5 diolefins | 109 |
| C5 cyclo-olefins | 19 |
| C5 cyclo sat's | 0.6 |
| C5 olefins (other) | 66 |
| C5 saturates (other) | 26 |
| C6 cyclodiolefins | 40 |
| C6 cyclo-olefins | 8.6 |
| C6 cyclo-olefins | 50 |
| C6 olefins (other) | 23 |
| C6 saturates (other) | 19 |
| Benzene | 270 |
| C7 olefins | 60 |
| C7 saturates | 40 |
| Toluene | 192 |
| C8 olefins | 27 |
| C8 saturates | 24 |
| Ethylbenzene | 81 |
| Xylenes (mixed) | 91 |

Example 2

This example shows that a mixture of benzene and toluene can be alkylated with methanol to produce xylenes, especially para-xylene. The catalyst comprised 10 wt % ZSM-5 zeolite having a $SiO_2/Al_2O_3$ molar ratio of 450 and containing 2.9 wt % phosphorous, wherein the catalyst was bound with clay and had been steamed for 0.75 hours at 1025° C. under 1 atmosphere of steam. The catalyst had median particle size of 66 μm and was loaded into a ⅜" external diameter quartz reactor. The feed streams included (1) a stream of a mixture of 50 mol % toluene and 50 mol % benzene; (2) methanol; and (3) steam. The aromatics to methanol molar (or weight) ratio was 4:3 and the hydrocarbon to steam molar ratio was 1:2. The reaction was conducted at 590° C., 35 psia, and 8 WHSV. Test results are presented in Table 3. It will be seen that the xylenes yield was 31.8%, of which 98.5% was para-xylene. Benzene conversion was 37.6% and toluene conversion was 8.5%.

TABLE 3

| | |
|---|---|
| Benzene:Toluene (mol) | 1:1 |
| (Benzene + Toluene):MeOH (mol) | 4:3 |
| H20:HC (H20 | 2:1 |
| Time on Stream (hr) | 0.3 |
| Toluene Conversion (%) | 8.5 |
| Benzene Conversion (%) | 37.6 |
| MeOH Conversion (%) | 95.9 |
| Xylene Yield on Toluene and Benzene (%) | 31.8 |
| Para-xylene Selectivity (%) | 98.5 |

Example 3

This example shows that a mixture of ethylbenzene and toluene can be reacted with methanol to produce xylenes, especially para-xylene. The catalyst comprised 10 wt % ZSM-5 zeolite having a $SiO_2/Al_2O_3$ molar ratio of 450 and containing 2.9 wt % phosphorous, wherein the catalyst was bound with clay and had been steamed for 0.75 hours at 1025° C. under 1 atmosphere of steam. The catalyst had median particle size of 66 μm and was loaded into a ⅜" external diameter quartz reactor. The feed streams included (1) a stream of a mixture of 50 mol % toluene and 50 mol % ethylbenzene; (2) methanol; and (3) steam. The aromatics to methanol molar ratio was 2:1 and the hydrocarbon to steam molar ratio was 1:2. The reaction was conducted at 590° C., 35 psia, and 2 WHSV. Test results are presented in Table 4. It will be seen that the xylenes yield was 20.2%, of which 94.8% was para-xylene. Ethylbenzene conversion was 61.2% and toluene conversion was 14.1%.

TABLE 4

| | |
|---|---|
| Ethylbenzene:Toluene (mol) | 1:1 |
| (Ethylbenzene + Toluene):MeOH (mol) | 2:1 |
| H2O:HC (H2O | 2:1 |
| Time on Stream (hr) | 3 |
| Toluene Conversion (%) | 14.1 |
| Ethylbenzene Conversion (%) | 61.2 |
| MeOH Conversion (%) | 99.9 |
| Xylene Yield on Toluene and Benzene (%) | 20.2 |
| Para-xylene Selectivity (%) | 94.8 |

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of" may be substituted therefor.

What is claimed is:

1. A hydrocarbon upgrading process comprising:
   (a) treating a hydrocarbon feed in at least one of a steam cracker, catalytic cracker, coker, hydrocracker, and reformer under suitable conditions to produce a first stream comprising olefinic and aromatic hydrocarbons;
   (b) recovering from said first stream a second stream composed mainly of $C_4$ to $C_{12}$ olefinic and aromatic hydrocarbons where the second stream contains less than 20 wt % of $C_3-$ and $C_{12}+$ hydrocarbons;
   (c) feeding said second stream and a methylating agent to a reaction zone containing a catalyst under reaction conditions including a temperature of about 450° C. to about 700° C., such that aromatics components in the second stream undergo dealkylation, transalkylation and/or methylation and aliphatic components undergo cracking and aromatization to produce a third stream having an increased xylene content compared with said second stream and a $C_3-$ olefin by-product;
   (d) recovering the $C_3-$ olefin by-product; and
   (e) recovering at least para-xylene from at least part of said third stream.

2. The process of claim 1, wherein the hydrocarbon feed is selected from natural gas liquids, natural gas condensate, naphtha, distillate, gas oils, crude oil, and/or resids.

3. The process of claim 1, wherein the methylating agent in (c) comprises methanol.

4. The process of claim 1, wherein the catalyst in (c) comprises a molecular sieve having a Constraint Index less than 3.

5. The process of claim 4, wherein the catalyst in (c) comprises zeolite Y or zeolite beta.

6. The process of claim 4, wherein the catalyst in (c) further comprises a molecular sieve having a Constraint Index of about 3 to about 12.

7. The process of claim 5, wherein the catalyst in (c) further comprises an MFI zeolite.

8. The process of claim 1, wherein the second stream is composed mainly of $C_4$ to $C_8$ olefinic and aromatic hydrocarbons and the catalyst in (c) comprises a molecular sieve having a Constraint Index of about 3 to about 12.

9. The process of claim 8, wherein said catalyst in (c) comprises an MFI zeolite.

10. The process of claim 9, wherein said MFI zeolite is phosphorus stabilized.

11. The process of claim 10, wherein said MFI zeolite has been selectivated so as to have an equilibrium sorption capacity for xylene of at least 1 gram per 100 grams of zeolite measured at 120° C. and a xylene pressure of 4.5±0.8 mm of mercury and an ortho-xylene sorption time for 30% of its equilibrium ortho-xylene sorption capacity of greater than 1200 minutes.

12. The process of claim 1, wherein said catalyst in (c) is substantially free of hydrogenation metal.

13. The process of claim 1, wherein said reaction conditions in (c) include a temperature of about 550° C. to about 620° C.

14. The process of claim 1, wherein said reaction conditions in (c) include a pressure of about 70 kPaa to about 700 kPaa.

15. The process of claim 1, wherein (c) is carried out in a moving bed reactor.

16. The process of claim 1, wherein (c) is carried out in a fluid bed reactor.

17. The process of claim 16, wherein part of the catalyst is removed from the reactor and circulated to an oxidative regenerator.

18. The process of claim 17, wherein additional fuel is added to the regenerator to heat the catalyst to provide a portion of the heat of reaction for step (c).

19. The process of claim 1, further comprising removing $C_4+$ olefins and saturated aliphatics from the third stream and recycling said $C_4+$ olefins and saturated aliphatics to (c).

20. The process of claim 1, further comprising removing benzene and/or toluene from the third stream and recycling said benzene and/or toluene to (c).

21. The process of claim 1, further comprising recovering benzene from the third stream.

22. The process of claim 1, further comprising removing a $C_8$ stream from the third stream and recovering para-xylene from said $C_8$ stream in (e).

23. The process of claim 22, wherein recovering para-xylene from said $C_8$ stream is affected in a crystallization and/or adsorption unit and also produces a para-xylene depleted stream.

24. The process of claim 23, wherein the para-xylene depleted stream is isomerized to equilibrium and the equilibrated stream is recycled to the crystallization and/or adsorption unit to recover para-xylene therefrom.

25. The process of claim 1 wherein when a steam cracker is employed as the process unit, the second hydrocarbon stream is a pyrolysis gasoline containing from about 15 wt % to about 65 wt % benzene, from about 5 wt % to about 35 wt % toluene, from about 1 wt % to about 15 wt % of $C_8+$ aromatic compounds and up to 50 wt %, non-aromatics.

* * * * *